United States Patent
Adkins, Jr. et al.

(10) Patent No.: US 10,993,922 B2
(45) Date of Patent: *May 4, 2021

(54) TOPICAL SKIN CARE COMPOSITIONS

(71) Applicant: OCuSOFT, Inc., Rosenberg, TX (US)

(72) Inventors: Nat Adkins, Jr., Richmond, TX (US); Troy Smith, Richmond, TX (US)

(73) Assignee: OCUSOFT, INC., Rosenberg, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,337

(22) Filed: Jan. 31, 2020

(65) Prior Publication Data

US 2020/0163909 A1  May 28, 2020

Related U.S. Application Data

(63) Continuation of application No. 16/295,617, filed on Mar. 7, 2019, now Pat. No. 10,576,048.

(60) Provisional application No. 62/640,848, filed on Mar. 9, 2018.

(51) Int. Cl.

| | |
|---|---|
| *A61K 36/00* | (2006.01) |
| *A61K 31/166* | (2006.01) |
| *A61K 36/889* | (2006.01) |
| *A61K 31/665* | (2006.01) |
| *A61K 36/886* | (2006.01) |
| *A61K 36/58* | (2006.01) |
| *A61K 8/04* | (2006.01) |
| *A61Q 19/00* | (2006.01) |
| *A61K 36/36* | (2006.01) |

(52) U.S. Cl.
CPC .............. *A61K 31/166* (2013.01); *A61K 8/04* (2013.01); *A61K 31/665* (2013.01); *A61K 36/36* (2013.01); *A61K 36/58* (2013.01); *A61K 36/886* (2013.01); *A61K 36/889* (2013.01); *A61Q 19/00* (2013.01)

(58) Field of Classification Search
CPC .................................................. A61K 36/00

USPC .......................................................... 424/725
See application file for complete search history.

(56) References Cited

U.S. PATENT DOCUMENTS

| | | | |
|---|---|---|---|
| 2002/0013361 A1 | 1/2002 | Perricone | |
| 2007/0003509 A1 | 1/2007 | Farwick et al. | |
| 2009/0117061 A1 | 5/2009 | Gross | |
| 2009/0269290 A1* | 10/2009 | Patnode | A61K 8/347 424/59 |
| 2015/0342852 A1 | 12/2015 | Van Den Nest et al. | |

FOREIGN PATENT DOCUMENTS

| | | |
|---|---|---|
| WO | 2006085907 A2 | 8/2006 |
| WO | 2013149323 A1 | 10/2013 |
| WO | 2017176246 A1 | 10/2017 |

* cited by examiner

*Primary Examiner* — Michael V Meller
(74) *Attorney, Agent, or Firm* — D'Ambrosio & Menon, PLLC; Usha Menon

(57) ABSTRACT

Compositions and methods for treating skin redness. According to an embodiment, the invention is a topical skin care composition having a dermatologically acceptable vehicle, such as, water and a plurality of ingredients dissolved in the vehicle. The ingredients include: a blend of natural oils; a plurality of vitamins; and 0.1-1 wt % salicyloyl phytosphingosine. The composition is unsuitable for application on the eyelids or eye area. The blend of natural oils includes: *Aloe barbadensis* leaf juice extract; *Cocos nucifera* (coconut oil); hydrolyzed glycosaminoglycans; and caprylic/capric triglycerides. The plurality of vitamins is selected from a group consisting of vitamin C, vitamin E, salts/derivatives of vitamin C and vitamin E, and mixtures thereof. In one aspect, the plurality of vitamins includes: sodium ascorbyl phosphate; disodium lauriminodipropionate tocopheryl phosphate; and jojoba oil.

1 Claim, No Drawings

TOPICAL SKIN CARE COMPOSITIONS

CROSS REFERENCE TO RELATED APPLICATION

This application is a continuation of U.S. patent application Ser. No. 16/295,617 filed on Mar. 7, 2019, and entitled TOPICAL SKIN CARE COMPOSITIONS, which claims the benefit of U.S. Provisional Patent Application No. 62/640,848 filed Mar. 9, 2018, and entitled "ANTI-REDNESS COMPOSITION AND METHODS FOR TREATING SKIN REDNESS," the entire contents and disclosures of which, both express and implied, is incorporated herein by reference.

TECHNICAL FIELD

The invention relates generally to the field of topically applied formulations used to treat skin redness

BACKGROUND

Redness of the skin is a common condition. It may be caused by rosacea, skin allergy, use of certain skin care products or treatments, cosmetic procedures, exercise and, in some cases, underlying diseases. Rosacea, for example, causes redness and visible blood vessels in the face. It may also produce small, red, pus-filled bumps. These signs and symptoms may flare up for a period of weeks to months and then diminish for a while. While the redness may not always be a cause for concern, it may be embarrassing, irritating and uncomfortable for the person suffering from this skin condition.

Anti-redness creams are commonly used to stop irritation and moisturize the skin. However, not all anti-redness creams are effective or include a blend that can treat the underlying cause of skin redness. Some anti-redness creams include steroids and other ingredients that could cause thinning of the skin if used daily for many consecutive weeks. Some moisturizers are instable and cause skin-irritation or have insufficient moisturization capabilities.

Accordingly, there is a need for stable compositions which reduce skin redness and inflammation of the skin. The compositions should not involve steroids or other similar substances. The compositions should also moisturize and calm the skin without causing any irritation or other harmful side effects.

SUMMARY

According to an embodiment, the invention is a topical skin care composition having a dermatologically acceptable vehicle, such as, water and a plurality of ingredients dissolved in the vehicle. The ingredients include: a blend of natural oils; a plurality of vitamins; and 0.1-1 wt % salicyloyl phytosphingosine. The composition is unsuitable for application on the eyelids or eye area. The blend of natural oils includes: *Aloe barbadensis* leaf juice extract; *Cocos nucifera* (coconut oil); hydrolyzed glycosaminoglycans; and caprylic/capric triglycerides. The plurality of vitamins is selected from a group consisting of vitamin C, vitamin E, salts/derivatives of vitamin C and vitamin E, and mixtures thereof. In one aspect, the plurality of vitamins includes: sodium ascorbyl phosphate; disodium lauriminodipropionate tocopheryl phosphate; and jojoba oil. The ingredients further include: (A) dried neem leaf extract (*Melia azadirachta*); and (B) an acetylated tetrapeptide. The ingredients further include a thickening agent. The thickening agent is selected from a group consisting of a polyacrylamide, a C13-14 isoparaffin, Laureth-7 and mixtures thereof. The ingredients further include salts of: (A) hyaluronic acid; and (B) glycyrrhizic acid.

In one aspect, the topical skin care composition includes: spray dried powdered *Aloe vera*; *Cocos nucifera* (coconut oil); dried neem leaf extract (*Melia azadirachta*); acetyl tetrapeptide-40; sodium hyaluronate; dipotassium glycyrrhizate; about 0.2 wt % salicyloyl phytosphingosine; sodium ascorbyl phosphate; and water. The composition further includes a thickening agent selected from a group consisting of a polyacrylamide, a C13-14 isoparaffin, Laureth-7 and mixtures thereof. The composition further includes hydrolyzed glycosaminoglycans. The composition includes disodium lauriminodipropionate tocopheryl phosphate.

The compositions are in a form selected from the group consisting of lotions, creams, serums, gels, sticks, sprays, ointments, liquid washes, foams and mousses. The compositions have a viscosity of 30,000-50,000 cPs at 25 degrees C. The compositions have a pH between 4.5-6.0.

In another embodiment, a method for treating a person having skin redness involves: administering an effective amount of the topical skin care composition described herein; and allowing the composition to remain on the skin. In certain embodiments, the skin care composition can be allowed to remain on the skin as a leave on formulation without the need for rinsing it off. The composition can be administered for 60 days to cause a reduction in the skin redness. In one aspect, the method further involves pre-cleansing the skin with a non-comedogenic composition prior to the administration of the topical skin care composition.

In yet another embodiment, the invention is a kit comprising: (A) a first container, the first container containing an anti-redness composition, the anti-redness composition includes: about 7-12 weight % (wt %) of *Aloe barbadensis* leaf juice extract; about 3-9 wt % of *Cocos nucifera* (coconut oil); about 1-4 wt % vitamin E and/or a derivative of vitamin E; and about 0.1-1 wt % salicyloyl phytosphingosine; and (B) a second container, second container containing a second composition, the second composition is a non-comedogenic cleanser, the cleanser including: PEG-80 sorbitan laurate; sodium trideceth sulfate; cocamidopropyl hydroxysultaine; PEG-150 distearate; sodium lauroamphodiacetate; sodium laureth-13 carboxylate; and PEG-15 cocopolyamine.

DETAILED DESCRIPTION

The term and phrases "invention," "present invention," "instant invention," and similar terms and phrases as used herein are non-limiting and are not intended to limit the present subject matter to any single embodiment, but rather encompass all possible embodiments as described.

As used herein, all weight percentages (wt. %) are based on the total wt. % of the skin care composition, unless otherwise specified. Additionally, all composition percentages are based on totals equal to 100 wt. %, unless otherwise specified.

The compositions and methods for their use can "comprise," "consist essentially of," or "consist of" any of the ingredients or steps disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and can include the ingredients of the present invention and do not exclude other ingredients or elements described herein. The use of the word "a" or "an" when used in conjunction with the term "comprising" in the claims and/or the specification may mean "one," but it is also consistent with the meaning of "one or more," "at least one," and "one or more than one." As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the composition (as opposed to the degree of utility) is maintained.

All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. In one non-limiting embodiment the terms are defined to be within 5%, more preferably within 1%, and most preferably within 0.5%. The term "substantially" and its variations are defined as being largely but not necessarily wholly what is specified as understood by one of ordinary skill in the art, and in one non-limiting embodiment substantially refers to ranges within 0.5%-5%.

As used herein, the term "effective amount" of a composition refers to an amount sufficient to elicit the desired biological response. As will be appreciated by those of ordinary skill in this art, and effective amount of a substance may vary depending on such factors as the desired biological endpoint, the patient, etc. In some embodiments, a therapeutically effective amount of a composition is an amount that is sufficient, when administered to a subject suffering from or susceptible to a disease, disorder, and/or condition, to treat, inhibit, reduce, prevent, and/or delay the onset of one or more symptoms of skin redness and skin inflammation. The terms "treat" or "reduce" or any variation of these terms includes a measurable decrease in skin redness. For example, the effective amount/therapeutically effective amount of the composition to treat skin redness is the amount that alleviates, ameliorates, relieves, inhibits, prevents, delays onset of, reduces severity of and/or reduces incidence of one or more symptoms or features associated with skin redness and inflammation.

Skin care products are used to achieve healthy and attractive skin. The present invention provides topical skin care compositions containing salicyloyl phytosphingosine, natural oils and vitamins. The compositions can effectively reduce/improve redness, splotchy/blotchy appearance of the skin and inflammation. The compositions can promote an improvement in the texture of the skin, such as, skin elasticity, restore suppleness and reduce flaking thereby minimizing the signs of aging. Certain embodiments of the skin care compositions have anti-inflammatory properties, including anti-microbial and anti-fungal properties. The compositions further facilitate moisturizing of the skin to maintain the skin's natural balance.

As used herein, the term "skin care composition," "product," "composition," and similar terms, including plural terms, can be used interchangeably. Specifically, the term skin care composition includes compositions that can be rubbed, spread, introduced into, or otherwise applied to the skin, or any part thereof for reducing redness of the skin. The term "skin care composition" and other terms specifically includes topical compositions for application to human skin. The term "topical application" means to apply the skin care composition onto the surface of the skin.

The present invention addresses a problem that has not been adequately addressed in the prior art and provides a solution to that problem that is distinct from the prior art. Each ingredient (and its percentage) has been carefully selected to treat skin redness and irritation. Some of the embodiments particularly treat skin conditions caused by one or more microbes such as, *E. coli, P. aeruginosa, S. aureus, C. albicans, A. brasiliensis* and other microbes. The skin care composition can be used to reduce skin redness and inflammation due to rosacea, allergic reactions, exaggerated immune responses and cosmetic procedures. Preferably, the skin care compositions of the invention are configured to dry quickly and cleanly without leaving visible residue or significant stickiness after application of a normal amount on the skin. The skin care compositions are stable and are configured to avoid undue toxicity, incompatibility, or allergic response, when applied to the skin. Topical skin care compositions of the present invention can have a selected viscosity to avoid significant dripping or pooling after application to skin.

Advantageously, the skin care composition includes a dermatologically acceptable vehicle and one or more ingredients dissolved in the vehicle. The ingredients are selected such that they are compatible with and are stable within the selected vehicle. In one embodiment, the vehicle includes water. The water can be either distilled or deionized water. However, other suitable vehicles, such as, alcohol or propylene glycol can also be used. The dissolved ingredients include a blend of natural oils, a plurality of vitamins and a sphingoid lipid.

The natural oils or moisturizers can include, without limitation, *Aloe barbadensis* leaf juice or *Aloe vera, Cocos nucifera* (coconut oil), glycosaminoglycans, hydrolyzed glycosaminoglycans and caprylic/capric triglycerides. *Aloe vera* enhances the appearance of dry or damaged skin by reducing flaking and restoring suppleness. *Aloe* is typically obtained from the leaves of *Aloe* plants. *Aloe* improves wound-healing and skin inflammation. *Cocos Nucifera* (coconut) oil is a skin conditioning agent which promotes skin elasticity. Hydrolyzed glycosaminoglycans act as a moisturizing and conditioning agent. Hydrolyzed glycosaminoglycans bind with water efficiently and increase depth hydration, improving the elasticity and firmness of the skin. Caprylic/capric triglyceride is a skin conditioning agent derived from coconut oil.

The skin care composition further includes one or more vitamins or vitamin derivatives. For example, the composition can include sources of vitamins C and E such as ascorbic acid or a salt thereof, tocopheryl phosphates or tocopheryl acetates and *Simmondsia Chinensis* (Jojoba) seed oil. In one embodiment, the skin care composition includes sodium ascorbyl phosphate, disodium lauriminodipropionate tocopheryl phosphates (DLTP) and jojoba oil. Sodium ascorbyl phosphate provides vitamin C which is an essential nutrient required for collagen production, tissue repair, and for the synthesis of neurotransmitters. DLTP is isolated from Vitamin E. DLTP is used for acne treatment, scar treatment, rosacea treatment, and as a moisturizer, conditioner ingredient, sunscreen component, and for anti-aging. DLTP. It can effectively facilitate a decrease in skin redness and inflammation if applied to an irritated area and can reduce inflammation of the skin. Jojoba seed oil is a skin conditioning agent or emollient. It has anti-bacterial properties and contains Vitamin E.

The sphingoid lipid comprises an anti-bacterial, anti-inflammatory and anti-irritant agent, such as, phytosphingosine (PSG) or a derivative thereof. The term "anti-irritant", as used herein, is an agent that prevents or reduces soreness, roughness, or inflammation of a bodily part, such as, the skin. PSG is a water-binding agent that mimics the natural lipid layer of the outer epidermis for increased moisturizing throughout the day. PSG has anti-redness and skin firming properties and can inhibit microorganisms. Beneficially, PSG has both anti-bacterial and wound-healing properties and it acts as an anti-inflammatory at concentrations as low as 0.1%. In a specific aspect, the skin care composition includes PSG which is esterified with salicylic acid and its derivatives.

Salicyloyl PSG is a derivative of the naturally occurring skin-identical PSG which is covalently coupled with salicylic acid. Salicyloyl PSG and its derivatives contributes to minimizing the signs of aging by skin repair and skin renewal, prevention of loss of moisture from the skin, regulate epidermal cell growth, supporting epidermal cell differentiation, and apoptosis, improving the conditions of mature or photoaged dermis by boosting collagen synthesis and reducing its degradation, reinforcing the dermal-epidermal junction and soothing inflamed skin.

The skin care composition can advantageously include other ingredients such as, without limitations, *Melia azadirachta* leaf extract, hyaluronic acids or its salts thereof, glycyrrhizin or glycyrrhizic acid or glycyrrhizinic acid or its salts thereof, tocopherol and tocopherol esters.

*Melia azadirachta* (neem leaf) extract has pesticidal, nematicidal, fungicidal, bactericidal, anti-inflammatory, anti-tumor, astringent and other beneficial properties.

In one embodiment, the skin care composition includes sodium hyaluronate. Sodium hyaluronate acts as a lubricant on the skin by restoring moisture and aiding in prevention of friction or abrasion. It is a polysaccharide that is distributed widely in the extracellular matrix of connective tissue. Sodium hyaluronate can hold more water than any other natural substance—up to 1,000 times its weight in water. It can reach deep down into the dermis to combine with, maintain and attract water. It also promotes skin/blood microcirculation and nutrient absorption. Thanks to its super-sized hydrating properties, sodium hyaluronate can promote smoother, softer skin with decreased wrinkles and an all-around fuller appearance.

In one embodiment, the skin care composition includes dipotassium glycyrrhizinate or dipotassium glycyrrhizate (licorice root extract). It can enhance the appearance of dry or damaged skin by reducing flaking and restoring suppleness.

In one embodiment, the skin care composition includes an acetylated tocopherol such as, acetyl tetrapeptide-40. This reduces skin irritation and decreases the appearance of facial redness caused by exaggerated immune response and inflammation.

The skin care composition can further include one or more thickening agents. For example, without limitation, it can include polyacrylamide, C13-14 isoparaffin, laureth-7 and mixtures thereof. Polyacrylamide further binds the ingredients together and act to retain specific product on the skin. C13-14 isoparaffin can also work as a solvent for the other ingredients. Laureth-7 can function as a surfactant/emulsifying agent.

The skin care composition can also include other ingredients, such as, caprylyl glycol, butylene glycol, laureth-4 and phenoxyethanol. Caprylyl Glycol is an emollient with anti-microbial activity that acts as a preservative. Butylene glycol can also act as a solvent and viscosity decreasing agent. Laureth-4 acts as a surfactant cleansing and solubilizing agent. Phenoxyethanol is a preservative.

In one specific embodiment, the composition includes water, *Aloe barbadensis* leaf juice; *Cocos Nucifera* (coconut) oil; hydrolyzed glycosaminoglycans; caprylic/capric triglyceride; *Melia azadirachta* leaf extract; polyacrylamide; C13-14 isoparaffin; Laureth-7; disodium lauriminodipropionate tocopheryl phosphate; acetyl tetrapeptide-40; caprylyl glycol; butylene glycol; sodium hyaluronate; *Simmondsia chinensis* (Jojoba) seed oil; laureth-4; salicyloyl phytosphingosine; dipotassium glycyrrhizate; sodium ascorbyl phosphate; and phenoxyethanol.

In one embodiment, the composition includes about: 50-70 wt % distilled water, 7-12 wt % *Aloe barbadensis* leaf juice extract and preferably, spray dried *Aloe vera* powder; 3-9 wt % *Cocos Nucifera* (coconut) oil; 0.1-1 wt %, and preferably 0.2 wt % salicyloyl phytosphingosine; 2-7 wt % hydrolyzed glycosaminoglycans; 2-7 wt % caprylic/capric triglyceride and *Melia azadirachta* leaf extract; 2-7 wt % polyacrylamide, C13-14 isoparaffin and Laureth-7; 1-5 wt % disodium lauriminodipropionate tocopheryl phosphate; 1-3 wt % acetyl tetrapeptide-40 and caprylyl glycol; 1-3 wt % butylene glycol; 0.1-3 wt % sodium hyaluronate; 0.1-3 wt % *Simmondsia chinensis* (Jojoba) seed oil; 0.1-3 wt % laureth-4; 0.1-3 wt % dipotassium glycyrrhizate; 0.01-1 wt % sodium ascorbyl phosphate; 0.1-3 wt % phenoxyethanol and 0.1-1 wt % caprylyl glycol.

In one non-limiting embodiment, the skin care composition is an opaque, white to off-white viscous lotion having a characteristic odor. The skin care composition has a pH range between 4.5-5.5 at 25° C. Preferably, the skin care composition has a pH between 5.00 and 6.00. In certain embodiments, the skin care composition has a pH of 5.65. The skin care composition can have a viscosity of 30,000-50,000 cPs at 25° C. (Brookfield LVT; spindle TE at 6 rpm). Preferably, the skin care composition has a viscosity between 30,000 and 40,000 cPs. The specific gravity of the skin care composition is between 0.8000 and 1.100. Preferably, the specific gravity of the skin care composition is between 0.990 and 1.000.

The skin care composition is stable and can cause none to limited irritation (i.e., no or only limited and acceptable skin irritancy) when applied to the skin to treat skin redness. The skin care composition can be used to not only treat the source of most skin redness conditions, but also the resulting symptoms leading to improved patient compliance. It also has added anti-inflammatory properties for long term relief from symptoms. The term "stable" when applied to the compositions of the instant invention is defined as having a comparable color when the skin care composition is placed on a flat and inert surface (i.e., removed from its container) under normal ambient air and light conditions (i.e., air and light conditions as normally exist in the living room at home) when kept for at least one month at room temperature (about 25° C.). Other than the above-defined color stability, the stability of the skin care composition may further include, without limitations, physical stability (e.g., viscosity, odor, appearance, texture, etc.) and chemical stability.

The current skin care compositions can be made in a variety of ways, including in a continuous process or in a batch process in the ratios previously discussed. In a non-limiting example, laureth-4, coconut oil and jojoba oil can be heated together in one vessel while hot distilled water, spray dried *Aloe vera* powder, dipotassium glycyrrhizate, phenoxyethanol and salicyloyl phytosphingosine are heated and shear mixed together in a separate vessel. When these two mixtures are at 60-90 degrees C., the two mixtures are blended together using fast sweep mixing. The mixture is cooled by 15-20 degrees C. and the thickening agents, namely, polyacrylamide, C14-C14 isoparaffin and laureth-7, are added to the mixture and mixed well for about 5-15 minutes. Butylene glycol is next added to the mixture and mixed well. The mixture is further cooled by another 10-20 degrees C. The remaining ingredients, with the exception of sodium ascorbyl phosphate, are added to the cooled mixture. This is followed by mixing well for another 5-15 minutes. Finally, sodium ascorbyl phosphate (or a pre-mixed solution of sodium ascorbyl phosphate in distilled water) is added to the solution and mixed well for a further 5-15 minutes. The resulting composition can then be filtered using filter paper and/or membrane filters so that no visible residue is left.

The skin care composition can be administered by any means known in the art. Preferably, the composition is formulated as a topical preparation.

According to an embodiment, this invention is a method of treating red and irritated skin. The method involves topically applying an effective amount of the skin care compositions of the present invention to the face, neck and any affected area, as needed, of a person suffering from skin redness. The effective amount may generally include a small amount of the skin care composition. The skin care composition may be lightly rubbed on or around the affected area, especially to the skin of the face. In one embodiment, the method involves allowing the composition to remain on the skin for a finite amount of time. In certain embodiments, the skin care composition can be allowed to remain on the skin and does not have to be rinsed off. For optimal effect, the skin care composition can be used as part of a daily skin care regimen for between 30-90 days, and preferably for at least 60 days. In one or more embodiments, for maximum effect and results, the user may apply the composition to the affected area multiple times a day, for example, 2-3 times a day. Alternately, the skin care composition may be applied as needed. The skin care composition facilitates calming of irritated skin, moisturizes the skin, and causes a reduction in the redness and inflammation. The skin care composition can work immediately upon application to soothe red and irritated skin.

It is important to avoid applying the skin care composition to the eyes or areas around the eyes. The method further involves instructing the user to wash their hands well after application so that they do not touch the eye areas with fingers/fingertips that have residual medication on it. The user may be recommended to wear protective gloves when applying the composition and to use a mirror to avoid spreading the product into their eyes. In certain embodiments, the method further involves applying the skin care composition using a suitable applicator (in lieu of or in addition to using the fingers). Suitable applicators may include pads, brushes, swabs, sponges, puffs, roll-on applicators, and other such devices.

In certain embodiments, the method further involves pre-cleansing (or cleansing) the affected area(s) prior to application (or reapplication). The pre-cleansing may involve using a gentle, non-comedogenic cleanser. A small amount of the cleanser can be rubbed onto wet skin taking care to avoid the eye area. The skin is then rinsed thoroughly and patted dry. In certain embodiments, the cleanser may include a composition containing: water, PEG-80 sorbitan laurate, sodium trideceth sulfate, cocamidopropyl hydroxysultaine, PEG-150 distearate, sodium lauroamphodiacetate, sodium laureth-13 carboxylate, xanthan gum, PEG-15 cocopolyamine, sodium chloride, phenoxyethanol and potassium sorbate.

In yet another embodiment, the skin care compositions of the present invention used in the treatment or amelioration of skin redness and inflammation can be included in a kit. A kit can include a container. The container can be selected from a group consisting of a bottle, a dispenser, a pressurized container, a metal tube, a plastic tube, or other types of containers into which the compositions can be retained. The kit and/or container can include product indicia on its surface. The indicia, for example, can be a word, a phrase, an abbreviation, a picture, or a symbol.

The skin care composition is in a form selected from the group consisting of lotions, creams, serums, gels, sticks, sprays, ointments, liquid washes, foams and mousses. Accordingly, the container is configured to dispense a predetermined amount of the composition in any of the above-referenced forms. The container can have spray, pump, or squeeze mechanisms. Those skilled in the art will recognize that the kit can also include instructions for applying, using and maintaining the skin care compositions of the present invention.

In certain embodiments, the kit may further include a suitable applicator. The applicator may be selected from a group consisting of pads, brushes, swabs, sponges, puff and roll-on applicators. The kit can also include one or more pairs of protective gloves.

In certain other embodiments, the kit may include the first container containing the topical skin care composition of the present invention and a second container. The second container may be configured to retain and dispense a predetermined amount of the non-comedogenic cleanser described herein.

In certain embodiments, the kit may include the first container containing the topical skin care composition of the present invention and another container for retaining and dispensing an eyelid cleansing composition. The eyelid cleansing composition can comprise: (a) a mixture of antimicrobial agents that substantially eliminates at least seven bacterial strains, wherein the mixture includes polyaminopropyl biguanide, a 1,2-glycol, and a sphingoid lipid, wherein the sphingoid lipid is salicyloyl phytosphingosine; (b) a blended surfactant solution that maintains the eyelid cleansing composition at a pH between 5.5 and 7.5, wherein the blended surfactant solution has a foaming ability; (c) a foam stabilizer; and (d) a moisturizer. In yet another embodiment, the kit can include the first container containing the topical skin care composition of the present invention and one or more pre-moistened single use cleansing pads. The pads can be pre-impregnated with the eyelid cleansing composition. In yet another embodiment, the kit can include the first container containing the topical skin care composition of the present invention, a second container containing the eyelid cleansing and one or more pads for receiving the eyelid cleansing composition or the topical skin care composition. The pads can include a suitable fabric, such as, a lint-free fabric material, namely, rayon or another suitable material that can receive the eyelid cleansing composition or the topical skin care composition. The pads may be single use disposable pads. In one embodiment, one or more of the pads may be contained within a sealable container. In one aspect, the sealable container may comprise a box or a package. The package may be made of any suitable material including plastic or metal foil material.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

We claim:

1. A sealed container consisting essentially of water, *Aloe Barbadensis* Leaf Juice, *Cocos Nucifera* Oil, Hydrolyzed Glycosaminoglycans, Caprylic/Capric Triglyceride, *Melia azadirachta* Leaf Extract, Polyacrylamide, C13-14 Isoparaffin, Laureth-7, Disodium Lauriminodipropionate Tocopheryl Phosphates, Acetyl Tetrapeptide-40, Caprylyl Glycol, Butylene Glycol, Sodium Hyaluronate, *Simmondsia Chinensis* Seed Oil, Laureth-4, Salicyloyl Phytosphingosine, Dipotassium Glycyrrhizinate, Sodium Ascorbyl Phosphate, Phenoxyethanol and Caprylyl Glycol.

* * * * *